United States Patent [19]

Skurkovich

[11] Patent Number: 4,885,165

[45] Date of Patent: Dec. 5, 1989

[54] PRODUCTION OF ANTI-VIRAL AND ANTI-BACTERIAL AGENTS IN COMBINATION

[76] Inventor: Simon Skurkovich, 261 Congressional La., #709, Rockville, Md. 20852

[21] Appl. No.: 680,830

[22] Filed: Dec. 12, 1984

Related U.S. Application Data

[63] Continuation-in-part of Ser. No. 240,106, Mar. 3, 1981, abandoned.

[51] Int. Cl.$^4$ ................. A61K 45/02; A61K 39/395; A61K 39/42
[52] U.S. Cl. ................. 424/85.4; 424/85.8; 424/86; 424/87
[58] Field of Search ............ 424/85, 85.4, 85.8, 424/86, 87; 435/68

[56] References Cited

U.S. PATENT DOCUMENTS

| | | | |
|---|---|---|---|
| 2,526,961 | 10/1950 | Meier et al. | 424/85 |
| 3,975,344 | 8/1976 | Schwartz | 424/85 |
| 4,024,241 | 5/1977 | Levy | 424/85 |
| 4,049,794 | 9/1977 | Straub | 424/85 |
| 4,132,776 | 1/1979 | Jeter | 424/101 |
| 4,160,825 | 7/1979 | Sikes | 424/85 |
| 4,279,884 | 7/1981 | Bradwell et al. | 424/85 |
| 4,279,892 | 7/1981 | Ishida et al. | 424/85 |

*Primary Examiner*—Blondel Hazel
*Attorney, Agent, or Firm*—Wells & White

[57] ABSTRACT

This invention provides for administering to donor animals a substance that generates both anti-viral agents, such as interferon, in the blood and anti-bacterial or antitoxic antibodies. This is done at a certain time before recovery of plasma so that both the anti-viral substance (interferon), and anti-bacterial or antitoxic antibodies are substantially maximized. In the case of non-human animals the blood is recovered from animals to be slaughtered and plasma containing both the interferon and anti-bacterial (antitoxic/antibodies) is separated, thereby providing a significant quantity of scarce serum inexpensively.

18 Claims, No Drawings

PRODUCTION OF ANTI-VIRAL AND ANTI-BACTERIAL AGENTS IN COMBINATION

CROSS-REFERENCE TO RELATED APPLICATION

The present application is a continuation-in-part of application Ser. No. 240,106, filed Mar. 3, 1981 now abandoned.

BACKGROUND OF THE INVENTION

This invention relates to the production of serums effective to control disease and more particularly it relates to methods of obtaining anti-viral (e.g. interferon) and anti-bacterial products.

Interferon is now commercially produced outside the body by culturing cells and by recombinant DNA technique. The cost of producing and separating interferon in these ways is high, and also is a slow tedious process which hardly provides enough interferon to meet the demand. Conversely the obtaining of interferon-containing plasma from an animal after introducing in it an interferonogen and use of this plasma as interferon preparation is relatively simple.

It is known, as set forth in U.S. Pat. No. 4,049,794, of O. Straub, which issued on Sept. 20, 1977, for example, that interferon is generated for control of various viral diseases in warm blooded animals. Biomedicine, 1978, Vol. 29, pp. 227-228, reports that interferon is generated in the human organism after introduction of an interferonogen, that is, a substance which causes the interferon to be induced. A typical example of the treatment of animals with serums is described in U.S. Pat. No. 4,160,825, of D. Dikes, granted July 10, 1979.

Accordingly, there is a need to improve the methods of producing interferon and, in particular, there is a need to increase the efficiency of production of interferon by animal donors.

Also, it is known to the art to obtain anti-bacterial substances by different manufacturing procedures than interferon. In general, the interferon and anti-bacterial substances also are administered separately after being obtained.

It is known that in the treatment of viral diseases, such as influenza, in many instances, where the viral disease is controlled, the patient has the after-effects of bacterial infections such as staphylococcus. In such cases, the prophylactic or treatment administration of companion anti-viral and anti-bacterial substances can control not only the viral infection but also the bacterial infection.

SUMMARY OF THE INVENTION

It is, therefore, an object of the present invention to produce complex companion anti-viral and anti-bacterial substances in one manufacturing procedure which produces a single product with combined anti-viral/anti-bacterial characteristics.

According to the present invention, there is provided a method of obtaining a disease control product from a warm blooded donor animal comprising the steps of:

(a) administering to the donor animal a first substance for inducing in the blood stream of the animal an agent for controlling bacterial disease, and a second substance for inducing in the blood stream of the animal an agent for controlling viral disease, (b) awaiting an incubation period until a recoverable quantity of said product comprised of said two agents is generated, (c) extracting a blood substance from the donor animal, and (d) treating the extracted blood substance to recover the product.

The first substance may be one which induces anti-toxic or anti-bacterial antibodies.

The substance administered to the animal for producing an anti-viral agent (i.e., the "second substance") is preferably an interferonogen.

DESCRIPTION OF THE PREFERRED EMBODIMENTS

There are a variety of known interferonogens which can cause production of interferon including bacteria, endotoxins, phytohoemaglutinin, ribonucleic acids, Poly I:Poly C; Poly G:Poly C, live or inactivated viruses such as NDV (Newcastle Disease Virus), Tiloron, etc. The use of these typical substances in a donor animal causes generation of interferon obtainable in the form of plasma as has been reported in such articles as Interferon-Containing Plasma: The Preparation for Treatment of Viral Infections, *Biomedicine, supra.*

This invention, for the first time, provides a practical production method for obtaining, at low cost from donor animals, commercially usable quantities of disease control products with anti-viral and anti-bacterial characteristics.

It is a well established procedure that meat and fur-bearing animals are slaughtered. In many instances they are carefully groomed to provide prime furs and meat by penning and given special diets for a few days before slaughter. After slaughter, the blood has little value under normal procedures.

In a single production method in accordance with the invention, a complex product is produced with both anti-viral and anti-bacterial properties. In a preferred embodiment of the invention, animals to be slaughtered are administered, two to six weeks before slaughter, with a substance generating an anti-bacterial agent in the blood stream of the animal. Then, in this preferred method, and from three hours to three to five days before slaughter, a substance that generates an anti-viral agent such as interferon is administered to the same animal.

It should be noted that, when the interferonogen is introduced into the animal, the generation of interferon peaks, as a rule, in a period of from three hours to three to five days, depending on the inducer and species of animal. Thus, the culturing in the donor animals can be time-wise consistent with the slaughter program.

Also, even in meat-producing animals, such as poultry, sheep, cattle, and swine, there is no tainting of meat or problem in the animal donor program provided by this invention because the interferonogens of the killed virus type and certain inactivated bacterial substances have no pathogenic effect.

Plasma separated from the blood of the slaughtered animal has both anti-viral and anti-bacterial properties.

The procedure of collecting and processing the blood to separate plasma containing the anti-viral and anti-bacterial agents is simple, inexpensive and efficient as compared with culture production.

The plasma then may be dried or frozen for later use.

It is also possible to administer to the animal before slaughter a substance which will induce antitoxic antibodies in the blood of the animal.

Alternatively, the animal is administered interferonogen, and three to six hours before slaughter by a broad spectrum antibiotic. Thus, the plasma at slaughter will have both anti-viral (interferon) and peak levels of anti-bacterial (antibiotic) properties. Animals may not only be used as donors at slaughter but (1) periodically as a live animal donor, and (2) several times just prior to slaughter, during the period of the presence of high titres of interferon and antibodies in the blood, using plasmapheresis. This is mostly valuable in obtaining these preparations from cats, dogs, horses, and other high organized mammals.

Live donor warm blooded animals, including humans, can periodically give interferon containing plasma also containing anti-bacterial and/or anti-toxic anti-bodies, after repeated introductions of interferon inducers not earlier than two to three weeks after the previous introduction. This takes into account the tolerance to the interferon inducer remaining for a period of time after the administration of the inducer. However, there is significant advantage in the method of obtaining the products just prior to slaughter because animals are available, the entire quantity of blood may be used for derivation of plasma, as a by-product, and the process is most efficient in terms of cost and man hours as compared with other known procedures for obtaining these products.

The specific embodiments of the present invention include a method of obtaining a disease control product from a warm blooded donor animal comprising the steps of:

(a) administering to the donor animal a first substance for inducing in the blood stream of the animal an agent for controlling bacterial disease, and a second substance for inducing in the blood stream of the animal an agent for controlling viral disease, (b) awaiting an incubation period until a recoverable quantity of said product comprised of said two agents is generated, (c) extracting a blood substance from the donor animal, and (d) treating the extracted blood substance to recover the product.

This method also includes the option wherein the animal is other than homosapiens and includes the additional steps of preparing the donor animal for slaughter; administering said substances before slaughter to permit the incubation period; and recovering substantially all the blood from the donor animal at slaughter for treatment.

Particular use of the method is made wherein the second substance comprises an interferonogen.

In a particular embodiment, the first and second substances are administered at two different times so that the incubation period permits recovery of blood at one time with the anti-viral and anti-bacterial agents substantially maximized.

Another embodiment of the present invention has in mind the first substance to induce antistaphylococcus antitoxic antibodies (antistaphylococcus plasma and immunoglobulin).

In yet another embodiment, the first substance is one which induces antipseudomonas antitoxic antibodies (antipseudomonas plasma and immunoglobulin).

Another embodiment contemplated is a first substance which, upon administration, induces anticoli antitoxic antibodies (anticoli plasma).

The method of the present invention also includes the steps of obtaining plasma from the step of treating the blood substance and then freezing the plasma to preserve it.

Further, the present method includes the step of treating the blood substance comprising obtaining plasma containing the product from whole blood and additionally drying the plasma to preserve it.

In embodiments wherein interferonogen is administered to an animal, it is preferably administered from three hours to five days before the recovery step and the first substance is administered to the animal from two to six weeks before the interferonogen to thereby produce a substantial maximization of anti-viral and anti-bacterial agents in the blood stream at the time of the recovery step.

The method of the present invention also includes the additional steps of waiting a period in the order of at least two weeks after recovery of blood substance, and repeating the steps of the method.

A variation of the method of the present invention includes the steps of identifying and preserving the product as an autologous preparation for disease control of the specific donor animal.

The following specific examples further illustrate the present invention:

EXAMPLE 1

It is proposed in this Example to use as donors, animals shortly to be slaughtered so that their blood may be recovered at slaughter time and processed.

Thus, fur-bearing animals, sheep, cattle, swine, or poultry are treated with staphylococcus anatoxin which induces, as an antitoxic substance (antibodies) in the blood, antistaphylococcus plasma and immunoglobulin. After the appearance of high titers of antibodies in the blood from the bacterial substance, the animals are administered with an interferonogen, i.e., NDV, Poly I: Poly C; Poly G: Poly C, Tilorone, or other inducers. The interferonogen is administered per os, per rectum, subcutaneous, intraveneously, interperetoneum, or intramuscular, preferably three hours to three to five days prior to slaughter to permit the maximum levels of interferon in the blood to be produced.

The blood is recovered from the slaughtered animal and treated to provide a serum (plasma) with a combination of anti-viral and anti-bacterial characteristics.

EXAMPLE 2

The procedure of Example 1, wherein the substance causing a serum to be generated comprises staphylococcus anatoxin, and the resulting antitoxic substance produced in the blood is antistaphylococcus plasma and immunoglobulin.

EXAMPLE 3

The procedure of Example 1, wherein the substance causing a serum to be generated comprises pseudomonas anatoxin, and the resulting antitoxic substance is antipseudomonas plasma and immunoglobulin.

EXAMPLE 4

The procedure of Example 1, wherein the substance causing a serum to be generated comprises *E. coli* vaccine or anatoxin, and the resulting anti-bacterial substance is anticoli (anti-Escherichia) plasma and immunoglobulin.

EXAMPLE 5

The procedure of Example 1, wherein the substance causing a serum to be generated comprises staphylococcus vaccine, streptococci vaccine, or other bacterial vaccines and/or anatoxins.

EXAMPLE 6

This Example is the same as Examples 1 through 5 with the exception that blood is taken from the animals additionally prior to slaughter.

Plasma derived from the blood in Examples 1 through 6 is processed and purified to isolate the pure interferon alone, interferon in combination with different plasma proteins (e.g. albumen or globulins), or with the anti-bacterial products in concentrated form.

EXAMPLE 8

A practically healthy, warm-blooded animal undergoes the same procedures of Examples 1 through 7 (immunization with bacterial antigens and induction with interferonogen). Then, plasma containing interferon together with anti-bacterial and/or antitoxic antibodies is frozen or dried for prolonged storage. In the case of diseases or for the purpose of short-term prophylaxis of viral or viral-bacterial infection such plasma are used for the same individuum, from which it was previously obtained. Thus, they are received in an auto-system. It is most effective for the treatment and prophylaxis of flu in humans, and different viral diseases in highly valuable animals, i.e., dogs, racing horses, and others. It is widely known that autologous preparations are more effective and less dangerous.

What I claim is:

1. A method of obtaining a disease control product from a warm blooded donor animal comprising the steps of:
   (a) administering to the donor animal a first substance for inducing in the blood stream of the animal an antibody for controlling bacterial disease, and a second substance for inducing in the blood stream of the animal an interferon for controlling viral disease,
   (b) awaiting an incubation period until a recoverable quantity of said product comprised of said antibody and interferon is generated,
   (c) extracting a blood substance from the donor animal, and
   (d) treating the extracted blood substance to recover the product.

2. The method of claim 1, wherein the animal is other than homosapiens and includes the additional steps of: preparing the donor animal for slaughter, administering said substances before slaughter to permit the incubation period, and recovering substantially all the blood from the donor animal at slaughter for treatment.

3. The method of claim 1, wherein said second substance comprises an interferonogen.

4. The method of claim 2, wherein said second substance comprises an interferonogen.

5. The method of claim 1, wherein said first and second substances are administered at two different times so that the incubation period permits recovery of blood at one time with the antibody and interferon substantially maximized.

6. The method of claim 1, wherein the first substance induces antitoxic antibodies.

7. The method of claim 1, wherein the first substance is one which induces antistaphylococcus plasma and immunoglobulin.

8. The method of claim 1, wherein the first substance is one which induces antipseudomonas plasma and immunoglobulin.

9. The method of claim 1, wherein said first substance administered induces anticoli plasma and immunoglobulin.

10. The method of claim 1, including the steps of obtaining plasma from the step of treating the blood substances and then freezing the plasma to preserve it.

11. The method of claim 1, including the step of treating the blood substance comprising obtaining from whole blood plasma containing the product and additionally drying the plasma to preserve it.

12. The method of claim 3, wherein the interferonogen is administered to the animal from three hours to five days before the recovery step.

13. The method of claim 4, wherein the interferonogen is administered to the animal from three hours to five days before the recovery step.

14. The method of claim 12, wherein said first substance is administered to the animal from two to six weeks before the interferonogen to thereby produce a substantial maximization of antibody and inteferon in the blood stream at the time of the recovery step.

15. The method of claim 13, wherein said first substance is administered to the animal from two to six weeks before the interferonogen to thereby produce a substantial maximization of anti-viral and anti-bacterial agents in the blood stream at the time of the recovery step.

16. The method of claim 1, including the additional steps of waiting a period of at least two weeks after recovery of blood substance, and repeating the steps of claim 1.

17. The method of claim 1, including the steps of preserving the product as an autologous preparation for disease control of the specific donor animal.

18. The method of claim 1, wherein the first substance induces anti-bacterial antibodies.

* * * * *